US005851767A

United States Patent [19]
Stanbridge et al.

[11] Patent Number: 5,851,767
[45] Date of Patent: Dec. 22, 1998

[54] DETECTION OF PROKARYOTIC ORGANISM BY DNA HYBRIDIZATION

[75] Inventors: Eric J. Stanbridge, Corona Del Mar, Calif.; Ulf Gobel, Freiberg, Germany

[73] Assignee: The Regents of the University of California, Oakland, Calif.

[21] Appl. No.: 469,600

[22] Filed: Jun. 6, 1995

Related U.S. Application Data

[63] Continuation of Ser. No. 136,723, Oct. 14, 1993, abandoned, which is a continuation of Ser. No. 20,874, Feb. 19, 1993, abandoned, which is a continuation of Ser. No. 799,856, Nov. 27, 1991, abandoned, which is a continuation of Ser. No. 191,852, May 6, 1988, abandoned, which is a continuation of Ser. No. 707,725, Mar. 4, 1985, abandoned.

[51] Int. Cl.$^6$ ............................. C12Q 1/68; C07H 21/04
[52] U.S. Cl. ......................... 435/6; 536/24.3; 536/24.32; 435/91.2
[58] Field of Search ..................... 435/6, 91.2; 536/24.3, 536/24.32, 23.1

[56] References Cited

U.S. PATENT DOCUMENTS

| | | | |
|---|---|---|---|
| 4,302,204 | 11/1981 | Wahl et al. | 436/501 |
| 4,358,535 | 11/1982 | Falkow et al. | 435/5 |
| 4,416,988 | 11/1983 | Rubin | 435/91.51 |
| 4,699,877 | 10/1987 | Cline et al. | 435/6 |

FOREIGN PATENT DOCUMENTS

| | | |
|---|---|---|
| 1215904 | 12/1986 | Canada . |
| 0 076 123 | 4/1983 | European Pat. Off. . |
| 0 079 139 | 5/1983 | European Pat. Off. . |
| 0 120 658 | 10/1984 | European Pat. Off. . |
| 0 155 359 | 9/1985 | European Pat. Off. . |
| 0 155 360 | 9/1985 | European Pat. Off. . |
| WO 84/01174 | 3/1984 | WIPO . |
| WO84/02721 | 7/1984 | WIPO . |

OTHER PUBLICATIONS

Alwine, J. C., et al., "Method for detection of specific RNAs in agarose gels by transfer to diazobenzyloxymethyl–paper and hybridization with DNA probes", *Proc. Natl. Acad. Sci. USA*, 74(12):5350–5354 (1977).

Amikam, D., et al., "Ribosomal RNA genes in Mycoplasma", *Nucleic Acids Res.*, 10(14):4215–4222 (1982).

Balch, et al., "Methanogens: A New Perspective", *Micro. Rev.*, 43(2):260–96 (1979).

Brenner, D. J., et al., "Conservation of Transfer Ribonucleic Acid and 5S Ribonucleic Acid Cistrons in *Enterbacteriaceae*", *J. Bacteriology*, 129(3):1435–39 (1977).

Chattopadhysay, S. K., et al., "Ribosomal RNA Genes of *Neurospora*: Isolation and Characterization", *Proc. Natl. Acad. Sci. USA*, 69(11):3256–3259 (1972).

De Smedt, J. & J. de Ley, "Intra– and Intergeneric Similarities of *Agrobacterium* Ribosomal Ribonucleic Acid Cistrons," *Intl. J. Sys. Bac.*, 27(3):222–240 (1977).

De Smedt, J., et al., "Intra– and Intergeneric Similarities of Ribosomal Ribonucleic Acid Cistrons of Free–Living Nitrogen–Fixing Bacteria" *Intl. J. of Sys. Bact.*, 30(1):106–122 (1980).

Fox, G. E., et al., "Classification of methanogenic bacteria by 16s ribosomal RNA characterization," *Proc. Natl. Acad. Sci. USA*, 7(10):4537–41 (1977).

Fox, G.E., et al., "The Phylogeny of Prokaryotes", *Sci.*, 209:457–463 (1980).

Gibson, J., et al., "A Phylogenetic Analysis of the Purple Photosynthetic Bacteria", *Current Microbio.*, 3:59–64 (1979).

Gillis, M. & J. de Ley, "Intra–and Intergeneric Similarities of the Ribosomal Ribonucleic Acid Cistrons of *Acetobacter* and *Gluconobacter*", *Int. J. Sys. Bact.*, 30(1):7–27 (1980).

Gourse, R. L. & S. A. Gerbi, "Fine Structure of Ribosomal RNA III. Location of Evolutionarily Conserved Regions within Ribosomal DNA", *J. Mol. Biol.*, 140:321–339 (1980).

Gutell, R. R., "Comparative Anatomy of 16–S–like Ribosomal RNA", *Progress in Nucleic Acid Research*, 32:155–216 (1985).

Mordarski, M., et al., "Ribosomal Ribonucleic Acid Similarities in the Classification of *Rhodococcus* and Related Taxa", *J. General Microbio.*, 118:313–319 (1980).

Pechman, K. J. & C. R. Woese, "Characterization of the Primary Structural Homology between the 16S Ribosomal RNAs of *Escherichia coli* and *BAcillus Megaterium* by Oligomer Cataloging", *J. Molec. Evolution*, 1:230–240 (1972).

Sogin, S. J., et al., "Phylogenetic Measurement in Procaryotes by Primary Structural Characterization", *J. Molec. Evolution*, 1:173–184 (1972).

Stanbridge, E. J. & E. L. Schneider, "The Need for Non–Cultural Methods for the Detection of Mycoplasma Contaminants", *Dev. Biol. Stand.*, 37:191–200 (1976).

Woese, C.R., et al., "Procaryote Phylogeny. I. Concerning the Relatedness of *Aerobacter aerogenes* to *Escherichia coli*", *J. Mol. Evol.*, 3:293–299 (1974).

Woese, C. R., et al., "Conservation of primary structure in 16S ribosomal RNA", *Nature*, 254:83–86 (1975).

Woese, C. R., et al., "Phylogenetic analysis of the mycoplasmas", *Proc. Natl. Acad. Sci. USA* 77(1):494–98 (1980).

Woese, C. R., "Archaebacteria", *Scientific American*, 244:98–122 (1981).

Zablen, L. B., "Procaryotic Phylogeny by Ribosomal Ribonucleic Acid Sequence Homology", Thesis, University of Illinois at Urbana–Champaign (1976).

Purification and Sequence Analysis of Synthetic Oligodeoxyribonucleotides, by Ray Wu, Nai–Hu Wu, Zahre Hanna, Fawzy Georges and Saran Narang, pp. 135–151.

(List continued on next page.)

*Primary Examiner*—David Guzo
*Attorney, Agent, or Firm*—Fulbright & Jaworski L.L.P.

[57] ABSTRACT

Biological probes useful for detecting mycoplasmas or prokaryotes in general, or specific mycoplasma and eubacterial species are derived from the ribosomal RNA gene by selecting particular nucleotide sequences common to the class of organisms being detected.

63 Claims, 1 Drawing Sheet

OTHER PUBLICATIONS

Oligonucleotide Synthesis, A Practical Approach IRL Press, 1984, Chapter 1 entitled "an Introduction to Modern Methods of DNA Synthesis" Michael J. Gait, pp. 1–22.

An Alternate Method For Synthesis Of Double–Stranded DNA Segments, Journal of Biological Chemistry–vol. 257, No. 16, Aug. 25, pp. 9226–9229 (1982).

Stryer, Biochemistry, 1981, W.H. Freeman & Co, San Francisco, p. 577.

*Chemical Abstracts* vol. 102, No. 13, Apr. 1, 1985, p. 172, abst. #107280t, Goebel, Ulf et al "Comparative analysis of *Mycoplasma* ribosomal RNA operons".

Gen–Probe–"Mycoplasma T.C. Detection Kit"–Package Insert. (1984).

Gobel et al. (1985) Abstract presented at Meeting of American Society of Microbiologists, Las Vegas Nevada Mar. 5, 1985.

Amikam, Dorit et al., "Mycoplasmas (Mollicutes) Have a Low Number of rRNA Genes", *J. of Bacteriology*, Apr. 1984, pp. 376–378.

Bohnert, Hans et al., "Homologies Among Ribosomal RNA and Messenger RNA Genes in Choroplasts, Mitochondria and *E. coli*", *Molec. Gen. Genet.*, 179:539–545 (1980).

Bos, J.L., et al., "Three Different Mutations in Codon 61 of the Human N–ras Gene Detected by Synthetic Oligonucleotide Hybridization", *Nucleic Acids Research*, vol. 12, No. 23, 1984.

Britten, R.J. et al., "Repeated Sequences in DNA", *Science*, vol. 161, No. 3841, Aug. 9, 1968.

Caruthers, M.H., et al., "New Methods for Synthesizing Deoxyoligonucleotides", *Genetic Engineering*, vol. 4, pp. 1–17, Plenum Publishing Co. (1982).

Cunningham, M., "Spot Blot: A Hybridization Assay for Specific DNA Sequences in Multiple Samples", *Anal. Biochem.*, 128:415–421 (1983).

Doi, Roy et al., "Heterogeneity of the Conserved Ribosomal Ribonucleic Acid Sequences of *Bacilus Suntilis*", *J. Bacteriology*, vol. 92, No. 1, Jul., 1966, pp. 88–96.

Fox, George et al., "Comparative Cataloging of 16s Ribosomal Ribonucleic Acid: Molecular Approach to Procaryotic Systematics", *Int'l J. System. Bacter.*, vol. 27, No. 1, Jan. 1977, pp. 44–57.

Frydenberg, Jane et al., "The Sequence of 16SrRNA From Mycoplasma Strain PG50", *DNA*, vol. 4, No. 3, 1985.

Gobel, U. et al., "Cloned Mycoplasma Ribosomal RNA Genes for the Detection of Mycoplasma Contamination in Tissue Cultures", *Science*, 226:1211–1213 (1984).

Gray, Michael et al., "On the Evolutionary Descent of Organisms and Organelles: A Global Phylogeny Based on a Highly Conserved Structural Core in Small Subunit Ribosomal RNA", *Nucleic Acids Research*, vol. 12, No. 14, 1984.

Kafatos, Fotis et al., "Determination of Nucleic Acid Sequence Homologies and Relative Concentrations by a Dot Hybridization Procedure", *Nucleic Acids Research*, vol. 7, No. 6, 1979.

Kan, Yuet Wai et al., "Prenatal Diagnosis of a–Thalessemia", *New England J. of Medicine*, vol. 295, No. 21, pp. 1165–1167 (Nov. 18, 1976).

Ketttmann, Richard et al., "Leukemogenesis by Bovine Leukemia Virus: Proviral DNA Integration and Lack of RNA Expression of Viral Long Terminal Repeat and 3' Proximate Cellular Sequences", *Proc. Natl. Acad. Sci. USA*, vol. 79, pp. 2465–2469, Apr. 1982.

Kohne, D.E., "Virus Detection by Nucleic Acid Hybridization: Examination of Normal and ALS Tissues for the Presence of Poliovirus", *J. Gen. Virol.*, 56:223–233 (1981).

Leary, J.J., "Rapid and Sensitive Colorimetric Method for Visualizing Biotin–labled DNA probes hybridized to DNA or RNA Immobilized on Nitrocellulose: Bio–blots", *Proc. Nat'l Acad. Sci. U.S.A.*, 80:4045–4049 (1983).

Moore, Richard L., "Ribosomal Ribonucleic Acid Cistron Homologies Among Hyphomicrobium and Various Other Bacteria", *Can. J. Microbiol.*, vol. 23, pp. 478–481 (1977).

Moore, Richard L. and McCarthy, Brian J., "Comparative Study of Ribosomal Ribonucleic ACid Cistrons in Enterobacteria and Myxobacteria", *J. Bacter.*, vol. 94, No. 4, pp. 1066–1074 (Oct., 1967).

Mosley, S.L. et al., "Identification of Enterotoxigenic *Escherichia coli* by Colony Hybridization Using Three Enterotoxin Gene Probes", *J. Infect. Dis.*, vol. 145, No. 6, pp. 863–869 (Jun. 1982).

Razin, S. et al., "Detection of Mycoplasmas Infecting Cell Cultures by DNA Hybridization", In Vitro, vol. 20, No. 5, pp. 404–408 (May 1984).

Reff, Mitchell E. et al., "Phylogenetic Relationships Between Mycoplasmas and Other Procaryotes Based upon the Electrophoretic Behavior of Their Ribosomal Ribonucleic Acids", *Intl J. Sys. Bacteriol.*, vol. 27, No. 3, pp. 185–193 (Jul. 1977).

Richardson, C.C., "Polynucvleotide Kinase from *Escherichia Coli* Infected With Bacteriophage T4", *Procedures in Nucleic Acid Research*, (Canton, Gl. and Davies, D.R., eds), vol. 2, pp. 815–828, Harper and Row, New York, (1971).

Schneider, Edward and Stanbridge, Eric, "Comparison of Methods for the Detection of Mycoplasmal Contamination of Cell Cultures: A Review", In Vivo, vol. 11, No. 1, pp. 20–34 (1975).

Sanger, F. et al., "DNA Sequencing With Chain–Terminating Inhibitors", *Proc. Nat'l Acad. Sci. U.S.A.*, 74:5463–5467 (1977).

Sinclair, John H. and Brown, Donald D., "Retention of Common Nucleotide Sequences in the Ribosomal Deoxyribonucleic Acid of Eukaryotes and Some of their Physical Characteristics", *Biochemistry*, vol. 10, No. 14, pp. 2761–2769 (1971).

Stanbridge, Eric J., "A Reevaluation of the Role of Mycoplasmas in Human Disease", *Ann. Rev. Microbiol.*, 30:169–187 (1976).

Suggs, Sidney V. et al., "Use of Synthetic Oligonucleotides as Hybridization Probes: Isolation of Cloned cDNA Sequences for H7uman $B_2$–microglobulin", *Proc. Natl. Acad. Sci. USA*, vol. 78, No. 11, pp. 6613–6617 (Nov. 1981).

Sugino, Wesley M. et al., "Partial Nucleotide Sequence Similarity Within Species of Mycoplasma and achoplasma", *J. Genl. Microbio.*, 121:333–338 (1980).

Taylor, John M. et al., "Efficient Transcripition of RNA into DNA by Avian Sarcoma Virus Polymerase", *Biochemica et Biophysica Acta*, 442:324–330 (1976).

Taylor, J.M. et al., "Use of Specific Radioactive Probes to Study Transcription and Replication of the Influenza Virus Genome", *J. of Virology*, vol. 21, No. 2 (Feb. 1977).

Thomas, Patricia S., "Hybridization of Denatured RNA and small DNA Fragment Transferred to Nitrocellulose", *Proc. Natl. Acad. Sci. USA*, vol. 77, No. 9, pp. 5201–5205 (Sep. 1980).

Wirth, Dyann F. and Pratt, Diane McMahon, "Rapid Identification of Leishmania Species by Specific Hybridization of Kinetoplast DNA in Cutaneous Lesioins", *Proc. Natl. Acad. Sci. USA*, vol. 79, pp. 6999–7003 (Nov. 1982).

DETECTION OF PROKARYOTIC ORGANISM BY DNA HYBRIDIZATION

This is a continuation of Ser. No. 08/136,723 filed Oct. 14, 1993, now abandoned, which is a continuation of Ser. No. 08/020,874 filed Feb. 19, 1993, now abandoned, which is a continuation of Ser. No. 07/799,856 filed Nov. 27, 1991, now abandoned, which is a continuation of Ser. No. 07/191,852 filed May 6, 1988, now abandoned, which is a continuation of Ser. No. 06/707,725 filed Mar. 4, 1985, now abandoned.

This invention was made with Government support under Grant No. AI/AM 14096-01 with the National Institutes of Health and the University of California. The Government has certain rights in this invention.

FIELD OF THE INVENTION

This invention relates generally to the field of Biology, and more particularly to the fields of Biomedicine, Biochemistry and Molecular Biology.

BACKGROUND AND SUMMARY OF THE INVENTION

Mycoplasmas are a group of pathogenic microorganisms of the Class Mollicutes characterized by having a small size and lacking a cell wall. These microorganisms are among the smallest-known organisms capable of a free living existence, and are important pathogens in man, plants and animals. For example, atypical pneumonia and non-gonococcal urethritis are common mycoplasma infections in man. Mycoplasmas have also been associated with rheumatoid arthritis, spontaneous abortion, infertility and other genital tract diseases, and certain autoimmune disease states. Moreover, mycoplasmas are common contaminants in cell cultures. In biological research, mycoplasma contamination of tissue culture is a serious problem which demands constant monitoring.

Not surprisingly, these organisms are extremely fastidious and at present there are no cost-effective specific diagnostic procedures to determine the presence of mycoplasma infections. The most commonly-employed detection methods for mycoplasmas in clinical samples are serological and cultural. The serological methods are subject to false positives and the cultural methods are costly, time consuming and tedious. Many of the biochemical techniques in current usage for detection of microbial contaminants in cell cultures do not specifically detect mycoplasmas but rather indicate the presence of any prokaryote or simple eukaryote such as yeast and fungi, and some may even detect viruses. Such a test is advantageous if one is interested only in the knowledge that a microbial agent is present, but if one is searching for a suspected etiological agent of an animal or human disease it is obviously necessary to classify the agent as fully as possible.

Further, the above procedures are hampered by special problems. For example, there are apparently "non-cultivable" mycoplasmas which are not detected by conventional culture methods. In addition, in the case of immunofluorescence tests more than one antibody might be required to identify the particular organism since more than nine different mycoplasma species are common tissue culture contaminants. Also, DNA stains are not necessarily mycoplasma-specific.

Therefore, a simple, sensitive, specific, cost-effective, and rapid mycoplasma detection system has been a desideratum in the fields of diagnostic medicine and biological research.

The use of nucleotide sequence homology and nucleic acid hybridization kinetics has become a widely-employed technique for detecting various organisms in cells and cell cultures. However, prior to this invention reliable and specific DNA probes have not been available for mycoplasma detection.

The present invention proceeds by the use of specific mycoplasma ribosomal RNA gene fragments which are labeled or tagged by a variety of techniques, such as radioisotope labeling, biotin labeling, PEI-peroxidase conjugates, or fluorescent antibody tagging ELISA methods, for the specific and sensitive detection of mycoplasmas in clinical specimens, cells or cell cultures by DNA or RNA hybridization.

In one aspect of the invention, a DNA sequence from the 16S RNA gene of mycoplasma is provided, which includes a nucleotide sequence selected from the group consisting of AACACGTATC, CGAATCAGCTATGTCG, GAGGTT—AAC, ATCCGGATTTATT, TCTCAGTTCGGATTGA, AGGTGGTGCATGGTTG, TCCTGGCTCAGGAT, ATACATAGGT, AACTATGTGC, AATTTTTCACAATG, TCTCGGGTCT, TAGATATATG which code for mycoplasma ribosomal RNA (rRNA) where T represents thymine, G represent guanine, A represents adenine, C represents cytosine and - indicates a nucleotide deletion within the sequence with respect to the comparable sequence in *E. coli*. These fragments differ significantly from the 16S RNA gene of *E. coli*, and thus form the basis for mycoplasma-specific probes which are constituted of labeled nucleotide sequences complementary to the above.

In another aspect of the invention, identified DNA sequences of a 16S RNA gene are provided which include nucleotide sequences selected from the group consisting of ACGGGTGAGT, TAATACCGGCAT, TACGGGAGGCAGCAGT, GTGGGGAGCAAA, AGGATTAGATACCCT, CCGTAAACGAT, GAATTGACGGGG, CCCGCACAAG, GGTGGAGCATGT, TGTTGGGTTAAGTCCCGCAACGA, GGGATGACGT, ACGTGCTACAATG, CTAGTAATCG, TGTACACACCGCCCGTCA, AAGTCGTAACAAGGTA, and TGGATCACCTCCTT, which code for prokaryotic rRNA. These fragments represent regions within the 16S RNA gene that are identical for *E. coli* and all mycoplasmas examined. Universal probes for all prokaryotes are constituted of labeled nucleotide sequences complementary to these fragments. DNA sequences from the 5S RNA gene and the 23S RNA gene can similarly be used.

In general the invention comprises a method for determining the presence of a prokaryotic organism which contains a nucleic acid including a particular nucleotide sequence which is present in nucleic acids from prokaryotic organisms but absent in nucleic acids from eukaryotic organisms, which comprises contacting a medium which may contain a nucleic acid or nucleic acid fragment from said prokaryotic organism including said particular nucleotide sequence with an oligonucleotide, including a nucleotide sequence complementary to said particular nucleotide sequence, whereby said oligonucleotide hybridizes with any nucleic acid or nucleic acid fragment from said prokaryotic organism, including said particular nucleotide sequence which may be present in said medium, and detecting the presence of any nucleic acid or nucleic acid fragment hybridized with said oligonucleotide.

Other aspects of the invention concern the specific biological probes used for detecting mycoplasmas or prokaryotes in general in accordance with the above described process and the identification and production of such probes.

DESCRIPTION OF THE PREFERRED EMBODIMENTS

Figure 1:
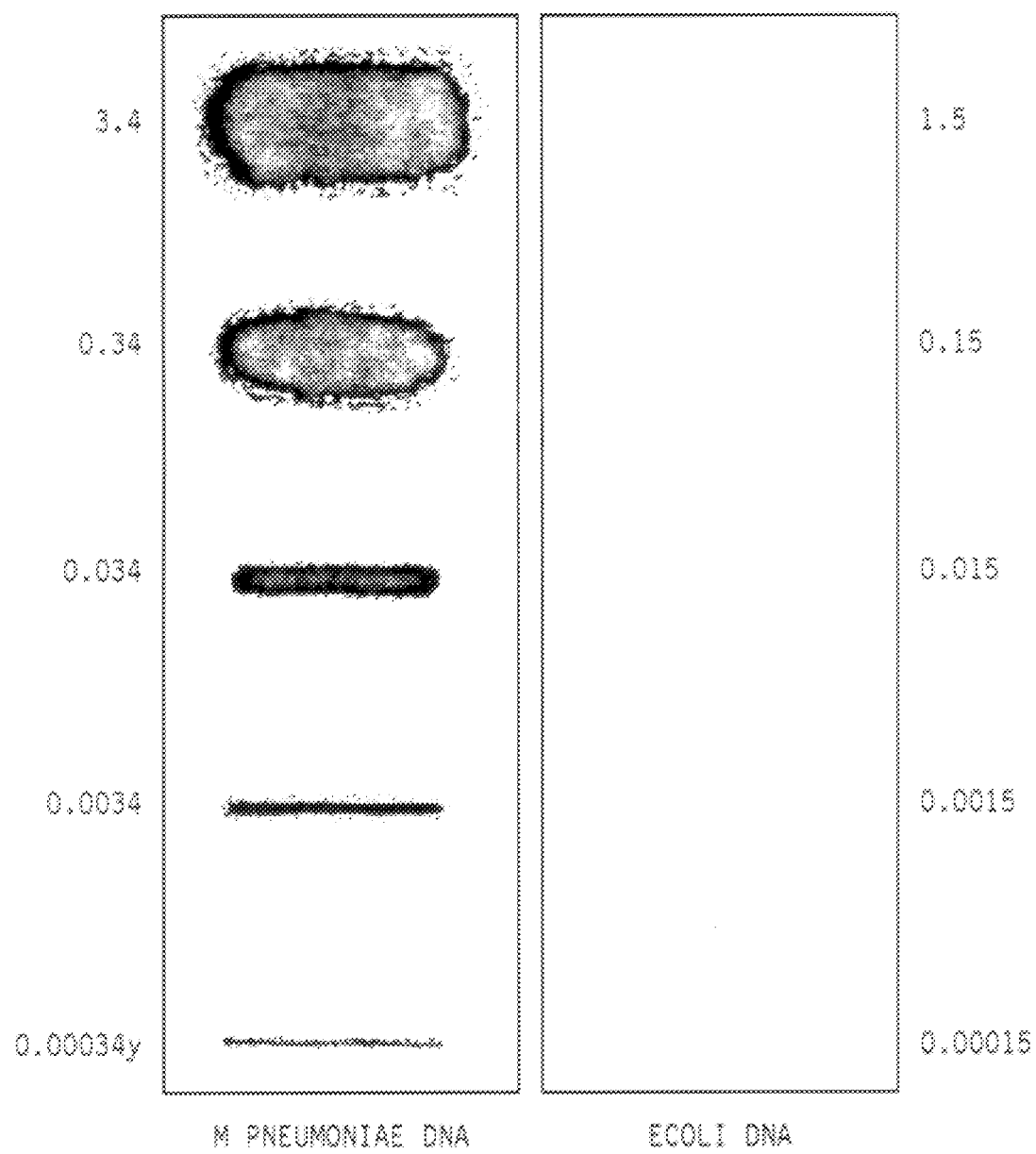
FIG. 1. The sole figure of the drawing shows a slot blot development illustrating the present invention.

The invention will now be described by detailing first the specific steps involved in producing and using the biological probes of the present invention and then describing how particular nucleotide sequences useful in this invention are determined.

SYNTHESIS OF DEOXYOLIGONUCLEOTIDES

The 16 bp deoxyoligonucleotide, GCTTAGTCGATACAGC, which is complementary to one of the 16S mycoplasma RNA gene sequences listed above, was synthesized using the phosphotriester solid phase procedure described in M. H. Caruthers et al., *Genetic Engineering*, Vol. 4, p. 1–17, Plenum Publishing Co. (1982), which is hereby incorporated by reference and which discusses the synthesis and isolation of dioxyoligonucleotides.

Any of the other deoxyoligonucleotides previously mentioned or any other desired oligonucleotide can be similarly prepared. For example, instead of a DNA probe it may be desired to synthesize an RNA probe such as a recombinant SP6 vector transcript containing the sequence CGAAUCAGCUAUGUCG.

DNA-RNA or RNA—RNA hybridization to ribosomal RNA molecules amplifies the sensitivity of the detection several hundredfold above any DNA—DNA or RNA-DNA hybridization using probes against genomic DNA sequences, since the use of such probe will detect multiple copies of ribosomal RNA per mycoplasma or eubacterial cell.

TESTING OF DEOXYOLIGONUCLEOTIDES

The above described deoxyoligonucleotide was $^{32}$P-labeled at the 5' end using the procedure in C. C. Richardson, *Procedures in Nucleic Acid Research* (Cantoni, G. L. and Davies, D. R., eds.), Vol. 2, pp. 815–828, Harper and Row, New York (1971), which is hereby incorporated by reference. The resulting labeled deoxyoligonucleotide was then used as a mycoplasma-specific probe. Specificity for mycoplasma was demonstrated by means of slot blot hybridization as described in M. Cunningham, *Anal. Biochem.* 128:415–421 (1983), which is herein incorporated by reference. For this purpose a 1600 bp DNA fragment of *Mycoplasma pneumoniae* which had been cloned into pUC8 was used. The 1600 bp fragment contains the above described 16 base deoxyoligonucleotide. A genomic digest of *E. coli*, a representative prokaryotic eubacterium, was also produced by digestion with the enzyme HindIII. The digested *E. coli* DNA and the 1600 bp *M. pneumoniae* DNA fragment were transferred onto nitrocellulose filters according to the procedure in the J. J. Leary et al., *Proc. Natl. Acad. Sci. U.S.A.* 80:4045–4049 (1983), which is hereby incorporated by reference. The nitrocellulose filters containing the DNA fragments were baked for 2 hours at 80° C. under reduced pressure and hybridized to the $^{32}$P-labeled deoxyoligonucleotide. Development of the resulting slot blots, shown in the drawing, revealed blots of increasing intensity for the *M. pneumoniae* DNA segment at 0.00034 ng, 0.0034 ng, 0.034 ng, 0.34 ng, and 3.4 ng (calculated for 16 bp) and no blots for the *E. coli* DNA segment at 0.00015 μg, 0.0015 μg, 0.015 μg, 0.15 μg, and 1.5 μg indicating the specificity of the deoxyoligonucleotide probe for mycoplasma. The deoxyoligonucleotide having the sequence GCTTAGTCGATACAGC thus is useful as a mycoplasma-specific probe which hybridizes with mycoplasmal DNA but does not hybridize with DNA of other prokaryotic organisms. On the other hand, a deoxyoligonucleotide having the sequence TGCCCACTCA, for example, which is complementary to one of the prokaryotic coding gene sequences, is useful as a prokaryote-specific probe which hybridizes with prokaryotes but not with eukaryotes.

For the detection of mycoplasmas in infected cells the following procedure has been found effective. The cells are trypsinized using 1–2 T75 tissue culture flasks with Trypsin EDTA (0.05% trypsin, 0.04% EDTA in PBS) for 2 minutes at 37° C. The trypsinized cells are resuspended in 1–2 ml of growth medium and spotted in a quantity of 50–100 μl ($1 \times 10^{5-1 \times 10^6}$ cells) onto a nitrocellulose filter wetted with 10×SSC (1×SSC: 15 mM Na citrate, 150 mM NaCl, pH 7.4) using a Minifold II slot blot hybridization apparatus available from Schleicher and Schuell, Inc., Keene, N.H. The DNA samples applied to the slot blots are denatured with alkali (0.5M NaOH, 1.5M NaCl) for 5–10 minutes at room temperature and neutralized for 5–10 minutes at room temperature using 0.5M Tris, pH 7.2 and 3.0M NaCl. The filter is then washed with 2×SSC for five minutes at room temperature and baked in a vacuum oven for 2 hours at 80° C. The filter is prehybridized for 2 hours at 65° C. using a prehybridization buffer consisting of 0.5 mM EDTA, 5 mM Tris, pH 7.5, 5×Denhardt, and 100 μg/ml heat denatured herring sperm DNA. Hybridization, using the probes of this invention in a concentration measured as 1–2×10$^6$ cpm of $^{32}$P-labeled deoxyoligonucleotide, specific activity>10$^8$ cpm/μg in hybridization buffer consisting of 10 mM Tris, pH 7.5, 1 mM EDTA, 0.75M NaCl, 1×Denhardt, 0.5% SDS, 10% dextran sulfate and 100 μg/ml heat denatured herring sperm DNA, is carried out at 65° C. for 16 hours. Following hybridization the filter is washed 2–4 hours at 65° C. with 2×SET, 0.2% SDS (1×SET:30 mM Tris, pH 8.0, 150 mM NaCl) and 1–2 hours at room temperature with 4 mM Tris base. The filter is then dried and exposed on X-ray film using 1 or 2 Dupont Cronex intensifying screens.

DETERMINATION OF PARTICULAR NUCLEOTIDE SEQUENCES

While the foregoing description of the present invention teaches how particular nucleotide sequences can be prepared and used, the broader scope of this invention may be realized by examining the techniques used for determining particular nucleotide sequences which are useful as mycoplasma-specific probes, probes specific for prokaryotes in general, probes specific for individual mycoplasma, ureaplasma, acholeplasma, and spiroplasma species or probes specific for individual eubacterial species.

Such determination involves the following steps:

1. cloning the entire genome of ribosomal RNA of a particular species of mycoplasma into a bacteriophage or plasmid vector;

2. probing the resulting ribosomal RNA gene fragments with a non-mycoplasma prokaryotic ribosomal RNA operon;

3. characterizing the fragments which hybridize with said non-mycoplasma prokaryotic ribosomal RNA operon;

4. identifying mycoplasma-specific fragments by differential hybridization as described in Gobel, U. and Stanbridge, E. J., *Science*, Vol. 226, pp. 1211–1213 (1984), which is hereby incorporated by reference and is described further below.

5. subcloning mycoplasma-specific fragments into a sequencing plasmid;

6. sequencing the resulting subcloned mycoplasma-specific fragments;

7. repeating steps 1–6 for other species of mycoplasma and for non-mycoplasmal prokaryotes; and 8. comparing sequences obtained in steps 6 and 7; whereby a sequence common to all the species of mycoplasma but differing from the corresponding sequence in non-mycoplasmal prokaryotes is useful as a mycoplasma-specific probe and a sequence common to all the species of mycoplasma, as well as the non-mycoplasmal prokaryotes, is useful as a probe specific for prokaryotes in general, and a sequence specific for either a specific mycoplasma, acholeplasma, ureaplasma, or spiroplasma species and sequences specific for any given eubacterial species, are useful as probes specific for individual mycoplasma, acholeplasma, ureaplasma, spiroplasma, or eubacterial species, respectively.

Cloning of the ribosomal RNA genome of *M. pneumoniae* was accomplished by HindIII digestion of total *M. pneumoniae* DNA and ligation of the HindIII fragments to the HindIII digested vector pUC8. The resulting ribosomal RNA gene fragments were probed with *E. coli* ribosomal RNA operon in the pKK 3535 plasmid according to the procedure in Gobel et al., *Science*, 226:1211–1213 (1984), which is hereby incorporated by reference, to identify cloned fragments which contained ribosomal sequences. There, we attempted to identify mycoplasmal DNA sequences that might account for these differences. A plasmid (pKK3535) that contains the entire rrnB operon of *E. coli* hybridized to six bands in Hind III—digested *M. hyorhinis* DNA. One of these bands, representing a 900-base-pair (bp) fragment from the 5'-terminal region of the *M. hyorhinis* 23S rRNA gene, disappeared when the hybridization was performed at higher temperatures, indicating a lower degree of homology between this particular fragment and the *E. coli* rrnB operon.

For further analysis, Hind III—digested *M. hyorhinis* DNA was cloned into the bacteriophage M13. Two clones, M13Mh129 and M13Mh171, contained inserts of 900 and 1200 bp in length, respectively, which hybridized to pKK3535. Mapping studies have shown that both fragments derive from the 23S rRNA gene (12). Both the 900- and 1200-bp fragments were purified and used as probes to identify rRNA gene (rDNA) fragments of representative Mycoplasma species: *M. arthritidis, M. fermentans, M. hominis, M. hyorhinis, M. pneumoniae,* and *Acholeplasma laidlawii.*

We found comparable hybridization among all species tested. Since the 900-bp fragment showed less homology than the 1200-bp fragment to the *E. coli* rrnB operon we did the converse experiment by hybridizing the M13Mh129 fragment to Hind III-digested *E. coli* DNA. Hind III-digested HeLa-cell DNA was included in this experiment, to determine the extent of homology between Mycoplasma rDNA and eukaryotic genomic and mitochondrial rRNA genes. There was substantial cross-hybridization between the *M. hyorhinis* 900-bp probe and genomic DNA fragments of the two Mycoplasma species included in this experiment. The extent of cross-hybridization to *E. coli* was negligible and no cross-hybridization at all was found to HeLa DNA. In addition, purified nick-translated HeLa mitochondrial DNA did not hybridize to *M. hyorhinis* DNA digests transferred to nitrocellulose filters. The same result was found when nick-translated M13Mh129 was used to probe mitochondrial DNA restriction fragments immobilized on nitrocellulose filters.

Having demonstrated the specificity of the Mycoplasma rDNA probe, we adapted a dot-blot hybridization procedure for the detection of mycoplasma infection in tissue culture using the nick-translated 900-bp Hind III fragment of M13Mh129 as probe. The assay detected less than 0.5 µg of homologous DNA. This corresponds to the amount of rDNA contained in less than $1\times10_5$ mycoplasmas, assuming the presence of one rRNA operon in a genome of about 800 kilobase pairs (kbp) in size. We obtained similar values by blotting a suspension of mycoplasma-infected cells onto nitrocellulose filters fewer than $1\times10_5$ mycoplasmas could be detected.

The results obtained with probe M13Mh129 show that it is specific for mycoplasmas and that the detection assay is quantitatively sensitive, ranking with the most sensitive indirect methods.

Here, a 1600 bp fragment was chosen on the basis of hybridization to mycoplasma species and not to *E. coli* or mammalian DNA under stringent hybridization conditions. This 1600 bp fragment was removed from the pUC8 vector by means of HindIII digestion and ligated to M13Mp8 DNA bacterial virus for sequencing using the Sanger dideoxy method described in Sanger et al., *Proc. Natl. Acad. Sci. U.S.A.*, 74:5463–5467 (1977), which is hereby incorporated by reference.

Comparison of the sequences of the mycoplasma species *M. pneumoniae, M. capricolum,* and *Mycoplasma species PG50* with *E. coli* indicated that certain sequences were common to all these species of mycoplasma but different from *E. coli*. These sequences could be synthesized and labeled and used as mycoplasma-specific probes. For example, GCTTAGTCGATACAGC constitued a mycoplasma-specific probe. Other sequences were common to these species of mycoplasma as well as *E. coli*. These latter sequences could be synthesized, labeled, and used as probes specific for all prokaryotic species. Still other sequences were unique to a single mycoplasma species and could be synthesized, labeled, and used as mycoplasma species-specific probes.

The present invention thus provides a specific, sensitive, and rapid method for the detection of mycoplasmas in contaminated cell cultures or other biological environments. Alternatively, the present invention can be used to provide a ribosomal DNA probe derived from a domain conserved in all prokaryotes. Such a probe would be extremely useful in the rapid and sensitive diagnosis of a bacteremia or septicemia in man or animals. The present invention may also be used to provide ribosomal DNA probes that are specific for individual mycoplasma, acholeplasma, ureaplasma, spiroplasma, and eubacterial species, respectively. These probes will be of particular use for those organisms where little or no information exists on their genetic make-up.

Although the present invention has been described in detail by reference to certain specific examples of deoxyoligonucleotides and mycoplasma species, it should be apparent to one skilled in the art that various modifications are possible. It is intended that this invention include such modifications and that the invention be limited only in accordance with the claims appended hereto.

What is claimed is:

1. A method for detecting the presence of mycoplasma specific nucleic acids, which comprises:

contacting a medium, which may contain a nucleic acid or nucleic acid fragment from said mycoplasma having said particular nucleotide sequence, with an oligonucleotide, said oligonucleotide comprising a nucleotide sequence complementary to said particular nucleotide sequence, whereby said oligonucleotide hybridizes with any nucleic acid or nucleic acid fragment from said mycoplasma which may be present in said medium; and detecting the presence of any nucleic acid or nucleic acid fragment hybridized with said oligonucleotide; wherein said particular nucleotide sequence includes at least one of the following mycoplasma-specific sequence regions or a sequence region, of at least nine nucleotides, complementary to at least one of the following sequences: 5'AACACGTATC3', 5'CGAATCAGCTATGTCG3', 5'GAGGTT-AAC3', 5'ATCCGGATTTATT3', 5'TCTCAGTTCGGATTGA3', 5'AGGTGGTGCATGGTTG3', 5'TCCTGGCTCAGGAT3', 5'ATACATAGGT3', 5'AACTATGTGC3', 5'AATTTTTCACAATG3', 5'TCTCGGGTCT3', and 5'TAGATATATG3', wherein T represents thymine, G represents guanine, A represents adenine, C represents cytosine and - indicates a nucleotide deletion within the sequence; wherein said oligonucleotide hybridizes with the nucleic acid or nucleic acid fragment from mycoplasma but not nucleic acids from eukaryotic or from other prokaryotic organisms, and wherein said oligonucleotide comprises at least nine nucleotides but is less than the length of mycoplasma rRNA or the nucleic acid sequence encoding mycoplasma rRNA.

2. A mycoplasma-specific probe, in a form which hybridizes to a particular nucleotide sequence, wherein said mycoplasma-specific probe is shorter than a mycoplasma rRNA or a nucleic acid sequence which encodes the mycoplasma rRNA, characterized in that it hybridizes with said particular nucleotide sequence, said particular nucleotide sequence comprising at least one of the following mycoplasma-specific sequence regions or a sequence region, of at least nine nucleotides, complementary to at least one of the following sequences: 5'AACACGTATC3', 5'CGAATCAGCTATGTCG3', 5'GAGGTT-AAC3', 5'ATCCGGATTTATT3', 5'TCTCAGTTCGGATTGA3', 5'AGGTGGTGCATGGTTG3', 5'TCCTGGCTCAGGAT3', 5'ATACATAGGT3', 5'AACTATGTGC3', 5'AATTTTTCACAATG3', 5'TCTCGGGTCT3', 5'TAGATATATG3' and a fragment of one of the foregoing sequence regions or the sequence region complementary thereto, wherein said fragment comprises at least nine nucleotides, wherein T represents thymine, G represents guanine, A represents adenine, C represents cytosine and - indicates a nucleotide deletion within the sequence, wherein said mycoplasma-specific probe hybridizes with the particular nucleotide sequence but not nucleotide sequences from eukaryotic or from other prokaryotic organisms.

3. A method for determining the presence of a prokaryotic organism which contains a nucleic acid having a particular nucleotide sequence which is present in nucleic acids from prokaryotic organisms but absent in nucleic acids from eukaryotic organisms, which comprises:

contacting a medium which may contain a nucleic acid or nucleic acid fragment from said prokaryotic organism with an oligonucleotide including a nucleotide sequence complementary to said particular nucleotide sequence, whereby said oligonucleotide hybridizes with any nucleic acid or nucleic acid fragment from said prokaryotic organism including said particular nucleotide sequence which may be present in said medium; and detecting the presence of any nucleic acid or nucleic acid fragment hybridized with said oligonucleotide, wherein said particular nucleotide sequence includes at least one of the following sequence regions or a sequence region, of at least ten nucleotides, complementary to at least one of the following sequences: 5'ACGGGTGAGT3', 5'TAATACCGCAT3', 5'TACGGGAGGCAGCAGT3', 5'GTGGGGAGCAAA3', 5'AGGATTAGATACCCT3', 5'CCGTAAACGAT3', 5'GAATTGACGGGG3', 5'CCCGCACAAG3', 5'GGTGGAGCATGT3', 5'TGTTGGGTTAAGTCCCGCAACGA3', 5'GGGATGACGT3', 5'ACGTGCTACAATG3', 5'CTAGTAATCG3', 5'TGTACACACCGCCCGTCA3', 5'AAGTCGTAACAAGGTA3', 5'TGGATCACCTCCTT3' and a fragment of any of the foregoing sequences wherein said fragment comprises at least ten nucleotides, wherein T represents thymine, G represents guanine, A represents adenine and C represents cytosine wherein said oligonucleotide hybridizes with nucleic acids from prokaryotic organisms but not nucleic acids from eukaryotic organisms.

4. A prokaryote-specific probe, shorter than a mycoplasma rRNA or a nucleic acid sequence which encodes the mycoplasma rRNA, wherein said probe hybridizes with a particular nucleotide sequence including at least one of the following prokaryotic sequence regions or a sequence region, of at least ten nucleotides, complementary to at least one of the following sequences: 5'ACGGGTGAGT3', 5'TAATACCGCAT3', 5'TACGGGAGGCAGCAGT3', 5'GTGGGGAGCAAA3', 5'AGGATTAGATACCCT3', 5'CCGTAAACGAT3', 5'GAATTGACGGGG3', 5'CCCGCACAAG3', 5'GGTGGAGCATGT3', 5'TGTTGGGTTAAGTCCCGCAACGA3', 5'GGGATGACGT3', 5'ACGTGCTACAATG3', 5'CTAGTAATCG3', 5'TGTACACACCGCCCGTCA3', 5'AAGTCGTAACAAGGTA3', 5'TGGATCACCTCCTT3' and a fragment of any of the foregoing sequences wherein said fragment comprises at least ten nucleotides, wherein T represents thymine, G represents guanine, A represents adenine and C represents cytosine wherein said prokaryote-specific probe comprises at least about ten nucleotides.

5. A method for identifying a particular nucleotide sequence for use as a probe specific for microorganisms from the class Mollicutes in general or for a given mycoplasma, ureaplasma, acholeplasma or spiroplasma species in particular, which method comprises:

a) cloning the entire operon of ribosomal RNA or portions thereof of a particular species of mycoplasma into a suitable vector;

b) probing the resulting ribosomal RNA gene fragments under preselected hybridization conditions with a non-mycoplasma prokaryotic ribosomal RNA operon or fragments thereof;

c) characterizing the fragments which hybridize under said preselected hybridization conditions with said non-mycoplasma prokaryotic ribosomal RNA operon or fragments thereof;

d) identifying mycoplasma-specific fragments by differential under said preselected hybridization conditions hybridization;

e) subcloning mycoplasma-specific fragments into a sequencing vector;

f) sequencing the resulting subcloned mycoplasma-specific fragments;

g) repeating steps a)–f) for other members of the Class Mollicutes;

h) comparing sequences obtained in steps f) and g); and i) identifying sequences common to all species of mycoplasma but differing from the corresponding sequences in non-mycoplasmal prokaryotes for use as mycoplasma-specific probes, or sequences specific for a given mycoplasma, ureaplasma, acholeplasma, or spiroplasma species for use as probes specific for individual species of mycoplasmas, ureaplasmas, acholeplasmas and spiroplasmas; or identifying for use as probes the sequences hybridizable to said mycoplasma-specific probes or probes specific for individual species of mycoplasmas, ureaplasmas, acholeplasmas and spiroplasmas; wherein said probes comprises at least nine nucleotides.

6. A method according to claim 5, wherein the robe is specific for a species of the genus Mycoplasma.

7. A method according to claim 5, wherein the probe is specific for a mycoplasma species selected from the group consisting of *Mycoplasma capricolum, Mycoplasma species PG*50 and *Mycoplasma pnezinioniae.*

8. A method according to claim 6, wherein the probe is specific for a particular species from a genus selected from the group consisting of ureaplasma, spiroplasma and acholeplasma.

9. A method for determining the presence of a prokaryotic organism of the class Mollicutes which contains a nucleic acid including a particular nucleotide sequence which is present in nucleic acids from said prokaryotic organisms but absent in nucleic acids from other prokaryotic organisms, which method comprises:

a) cloning the entire operon of ribosomal RNA or portions thereof of a particular species of mycoplasma into a suitable vector;

b) probing the resulting ribosomal RNA gene fragments under preselected hybridization conditions with a non-mycoplasma prokaryotic ribosomal RNA operon or fragments thereof;

c) characterizing the fragments which hybridize with said non-mycoplasma prokaryotic ribosomal RNA operon or fragments thereof;

d) identifying mycoplasma-specific fragments by differential hybridization under said preselected hybridization conditions;

e) subcloning mycoplasma-specific fragments into a sequencing vector;

f) sequencing the resulting subcloned mycoplasma-specific fragments;

g) repeating steps a)–f) for other members of the Class Mollicutes;

h) comparing sequences obtained in steps f) and g);

i) identifying sequences common to all species of mycoplasma but differing from the corresponding sequences in non-mycoplasmal prokaryotes for use as mycoplasma-specific probes, or sequences specific for a given mycoplasma, ureaplasma, acholeplasma, or spiroplasma species for use as probes specific for individual species of mycoplasmas, ureaplasmas, acholeplasmas and spiroplasmas;

j) contacting a medium which may contain a nucleic acid or nucleic acid fragment from said prokaryotic organism, having said particular nucleotide sequence, with an oligonucleotide including a nucleotide sequence identified in step i) complementary to said particular nucleotide sequence, under said preselected hybridization conditions whereby said oligonucleotide hybridizes with any nucleic acid or nucleic acid fragment from said prokaryotic organism including said particular nucleotide sequence which may be present in said medium; and k) detecting the presence of any nucleic acid or nucleic acid fragment hybridized with said oligonucleotide.

10. A method according to claim 9, wherein the probe is specific for a particular species from a genus selected from the group consisting of ureaplasma, spiroplasma and acholeplasma.

11. A method according to claim 9, wherein said nucleic acid including said particular nucleotide sequence is the 16S gene or a fragment thereof.

12. A method according to claim 9, wherein said nucleic acid including said particular nucleotide sequence is the 23S gene or a fragment thereof.

13. A method according to claim 9, wherein said particular nucleotide sequence is the 5S gene or a fragment thereof.

14. A method according to claim 9 wherein the probe is specific for a species of the genus Mycoplasma.

15. A method according to claim 9, wherein the probe is specific for a mycoplasma species selected from the group consisting of *Mycoplasma capricolum, Mycoplasma species PG*50 and *Mycoplasma pneumoniae.*

16. An oligonucleotide having the sequence 3'GCT-TAGTCGATACAGC5' or a sequence complementary to said sequence, wherein said oligonucleotide and said sequence complementary to it are each shorter than the gene encoding mycoplasma rRNA, and are each at least nine nucleotides in length.

17. An oligonucleotide having the sequence 5'CGAAU-CAGCUAUGUCG3' or a sequence complementary to said sequence, wherein said oligonucleotide and said sequence complementary to it are each shorter than the mycoplasma rRNA, and are each at least nine nucleotides in length.

18. A method for determining the presence in a medium of a mycoplasma specific nucleic acid sequence, comprising the steps of:

contacting the medium with an oligonucleotide, said oligonucleotide comprises a nucleotide sequence which is hybridizable to said mycoplasma specific nucleic acid sequence; and detecting the presence of the mycoplasma specific nucleic acid sequence hybridized with said oligonucleotide; wherein said oligonucleotide includes at least one of the following sequences or sequences, of at least nine nucleotides, complementary thereto: 5'AACACGTATC3', 5'CGAATCAGCTATGTCG3', 5'GAGGTT-AAC3', 5'ATCCGGATTTATT3', 5'TCTCAGTTCGGATTGA3', 5'AGGTGGTGCATGGTTG3', 5'TCCTGGCTCAGGAT3', 5'ATACATAGGT3', 5'AACTATGTGC3', 5'AATTTTTCACAATG3', 5'TCTCGGGTCT3', 5'TAGATATATG3', 5'AACACGUAUC3', 5'CGAAUCAGCUAUGUCG3', 5'GAGGUU-AAC3', 5'AUCCGGAUUUAUU3', 5'UCUCAGUUCGGAUUGA3', 5'AGGUGGUGCAUGGUUG3', 5'UCCUGGCUCAGGAU3', 5'AUACAUAGGU3', 5'AACUAUGUGC3', 5'AAUUUUUCACAAUG3', 5'UCUCGGGUCU3', and 5'UAGAUAUAUG3', and a fragment of any one of the foregoing sequences or their complementary sequences, wherein said fragment comprises at least nine nucleotides, wherein T represents thymine, G represents guanine, A represents adenine, C represents cytosine, U represents uracil, and - indicates a nucleotide deletion within the sequence wherein said oligonucleotide comprises at least nine nucleotides but is less than the length of mycoplasma rRNA or the nucleic acid sequence encoding mycoplasma rRNA.

19. A method for determining the presence of a prokaryotic organism in a medium, comprising the steps of:

contacting the medium which may contain a nucleic acid sequence from said prokaryotic organism with an oligonucleotide which hybridizes with the nucleic acid sequence of said prokaryotic organism; and detecting the presence of the nucleic acid sequence of said prokaryotic organism which hybridized with said oligonucleotide, wherein said oligonucleotide includes at least one of the following sequences of at least ten nucleotides, or sequences complementary to at least one of the following sequences: 5'ACGGGTGAGT3', 5'TAATACCGCAT3', 5'TACGGGAGGCAGCAGT3', 5'GTGGGGAGCAAA3', 5'AGGATTAGATACCCT3', 5'CCGTAAACGAT3', 5'GAATTGACGGGG3', 5'CCCGCACAAG3', 5'GGTGGAGCATGT3', 5'TGTTGGGTTAAGTCCCGCAACGA3', 5'GGGATGACGT3', 5'ACGTGCTACAATG3', 5'CTAGTAATCG3', 5'TGTACACACCGCCCGTCA3', 5'AAGTCGTAACAAGGTA3', 5'TGGATCACCTCCTT3',5'ACGGGUGAGU3', 5'UAAUACCGCAU3', 5'UACGGGAGGCAGCAGU3', 5'GUGGGGAGCAAA3', 5'AGGAUUAGAUACCCU3', 5'CCGUAAACGAU3', 5'GAAUUGACGGGG3', 5'CCCGCACAAG3', 5'GGUGGAGCAUGU3', 5'UGUUGGGUUAAGUCCCGCAACGA3', 5'GGGAUGACGU3', 5'ACGUGCUACAAUG3', 5'CUAGUAAUCG3', 5'UGUACACACCGCCCGUCA3', 5'AAGUCGUAACAAGGUA3', 5'UGGAUCACCUCCUU3' and a fragment of any of the foregoing sequences and their complementary sequences wherein said fragment comprises at least ten nucleotides, wherein T represents thymine, G represents guanine, A represents adenine and C represents cytosine, U represents uracil wherein said oligonucleotide comprises at least ten nucleotides but is less than the length of the prokaryote rRNA or the nucleic acid sequence encoding the prokaryote rRNA.

20. A composition comprising a synthesized and isolated oligonucleotide having the sequence 3'GCTTAGTCGATA-CAGC5' or a sequence complementary to said sequence, or fragments of the foregoing of between 10 to 16 nucleotides in length, wherein said oligonucleotide hybridizes to nucleic acid sequence of mycoplasma but not to nucleic acid sequence of another prokaryote or eukaryote.

21. A composition comprising a synthesized and isolated oligonucleotide having the sequence 5'CGAAUCAGC-UAUGUCG3' or a sequence complementary to said sequence, or fragments of the foregoing of between 10 to 16 nucleotides in length, wherein said oligonucleotide hybridizes to nucleic acid sequence of mycoplasma but not to nucleic acid sequence of another prokaryote or eukaryote.

22. A composition comprising a synthesized and isolated mycoplasma-specific probe, wherein said probe hybridizes with a particular nucleotide sequence, said particular nucleotide sequence comprises at least one of the following mycoplasma-specific sequence regions or a sequence region, of at least nine nucleotides, complementary to at least one of the following sequences: 5'AACACGTATC3', 5'CGAATCAGCTATGTCG3', 5'GAGGTT-AAC3', 5'ATCCGGATTTATT3', 5'TCTCAGTTCGGATTGA3', 5'AGGTGGTGCATGGTTG3', 5'TCCTGGCTCAGGAT3', 5'ATACATAGGT3', 5'AACTATGTGC3', 5'AATTTTTCACAATG3', 5'TCTCGGGTCT3', 5'TAGATATATG3', 5'AACACGUAUC3', 5'CGAAUCAGCUAUGUCG3', 5'GAGGUU-AAC3', 5'AUCCGGAUUUAUU3', 5'UCUCAGUUCGGAUUGA3', 5'AGGUGGUGCAUGGUUG3', 5'UCCUGGCUCAGGAU3', 5'AUACAUAGGU3', 5'AACUAUGUGC3', 5'AAUUUUUCACAAUG3', 5'UCUCGGGUCU3', 5'UAGAUAUAUG3', and a fragment of any one of the foregoing sequences or their complementary sequences, wherein said fragment comprises at least nine nucleotides, wherein T represents thymine, G represents guanine, A represents adenine, C represents cytosine, U represents uracil and - indicates a nucleotide deletion within the sequence, wherein said mycoplasma-specific probe hybridizes with the particular nucleotide sequence but not nucleotide sequences from eukaryotic or other prokaryotic organisms.

23. The composition of claim 22, wherein the mycoplasma-specific probe is labelled for detection.

24. A composition comprising a synthesized and isolated prokaryote-specific probe, wherein said probe hybridizes with a particular nucleotide sequence including at least one of the following prokaryotic sequence regions or a sequence region, of at least ten nucleotides, complementary to at least one of the following sequences: 5'ACGGGTGAGT3', 5'TAATACCGCAT3', 5'TACGGGAGGCAGCAGT3', 5'GTGGGGAGCAAA3', 5'AGGATTAGATACCCT3', 5'CCGTAAACGAT3', 5'GAATTGACGGGG3', 5'CCCGCACAAG3', 5'GGTGGAGCATGT3', 5'TGTTGGGTTAAGTCCCGCAACGA3', 5'GGGATGACGT3', 5'ACGTGCTACAATG3', 5'CTAGTAATCG3', 5'TGTACACACCGCCCGTCA3', 5'AAGTCGTAACAAGGTA3', 5'TGGATCACCTCCTT3', 5'ACGGGUGAGU3', 5'UAAUACCGCAU3', 5'UACGGGAGGCAGCAGU3', 5'GUGGGGAGCAAA3', 5'AGGAUUAGAUACCCU3', 5'CCGUAAACGAU3', 5'GAAUUGACGGGG3', 5'CCCGCACAAG3', 5'GGUGGAGCAUGU3', 5'UGUUGGGUUAAGUCCCGCAACGA3', 5'GGGAUGACGU3', 5'ACGUGCUACAAUG3', 5'CUAGUAAUCG3', 5'UGUACACACCGCCCGUCA3', 5'AAGUCGUAACAAGGUA3', 5'UGGAUCACCUCCUU3' and a fragment of any of the foregoing sequences or their complementary sequences, wherein said fragment comprises at least ten nucleotides, wherein T represents thymine, G represents guanine, A represents adenine C represents cytosine and U represents uracil.

25. The composition of claim 24, wherein the prokaryote-specific probe is labelled for detection.

26. A method for determining the presence of a prokaryotic organism in a medium, comprising the steps of:

contacting the medium which may contain a nucleic acid sequence from said prokaryotic organism with a synthesized and isolated oligonucleotide which under preselected hybridization conditions hybridizes with the nucleic acid sequence of said prokaryotic organism; and detecting the presence of the nucleic acid sequence of said prokaryotic organism which hybridized with said oligonucleotide, wherein said oligonucleotide comprises a section substantially complementary to the nucleic acid sequence of the prokaryotic organism such that under said preselected hybridization conditions said section hybridizes to the nucleic acid sequence of the prokaryotic organism but not to the nucleic acid sequence of a non-prokaryotic organism, said section being from nine nucleotides to twenty-three nucleotides. sequence but not to a non-mycoplasma-specific nucleic acid sequence.

27. The method of claim 26, wherein the prokaryotic organism is a mycoplasma and the oligonucleotide hybridizes to a mycoplasma-specific nucleic acid sequence but not to a non-mycoplasma-specific nucleic acid sequence.

28. A composition comprising a synthesized and isolated oligonucleotide which under preselected hybridization conditions hybridizes to a mycoplasma-specific nucleic acid sequence but not to a non-mycoplasma-specific nucleic acid sequence.

29. The substantially pure composition of claim 28, wherein the oligonucleotide comprises at least nine nucleotides.

30. The composition of claim 28, wherein the oligonucleotide comprises a section which under said preselected hybridization conditions is substantially complementary to the mycoplasma-specific nucleic acid sequence such as to allow the oligonucleotide to hybridize to the mycoplasma-specific nucleic acid sequence, said section comprises from nine to sixteen nucleotides.

31. A composition comprising a synthesized and isolated oligonucleotide which comprises a section substantially complementary to the nucleic acid sequence of a prokaryotic organism such that under preselected hybridization conditions said section hybridizes to the nucleic acid sequence of the prokaryotic organism but not to the nucleic acid sequence of a non-prokaryotic organism, said section being from nine nucleotides to twenty-three nucleotides.

32. The composition of claim 31, wherein the prokaryotic organism is a mycoplasma and under said preselected hybridization conditions the oligonucleotide hybridizes to a mycoplasma-specific nucleic acid sequence but not to a non-mycoplasma-specific nucleic acid sequence.

33. A composition comprising a synthesized and isolated oligonucleotide which comprises a section having a defined nucleic acid sequence substantially complementary to the nucleic acid sequence of a prokaryotic organism such that under preselected hybridization conditions said section hybridizes to the nucleic acid sequence of the prokaryotic organism but not to the nucleic acid sequence of a non-prokaryotic organism.

34. A composition comprising a synthesized and isolated oligonucleotide which comprises a section having a defined nucleic acid sequence substantially complementary to the nucleic acid sequence of a mycoplasma such that under preselected hybridization conditions said section hybridizes to the nucleic acid sequence of the mycoplasma but not to the nucleic acid sequence of an eukaryote or of another prokaryote.

35. A composition consisting essentially of an oligonucleotide having the sequence 3'GCTTAGTCGATACAGC5' or a sequence complementary to said sequence, or fragments of the foregoing of between 10 to 16 nucleotides in length, wherein said oligonucleotide hybridizes to nucleic acid sequence of mycoplasma but not to nucleic acid sequence of another prokaryote or eukaryote.

36. A composition consisting essentially of an oligonucleotide having the sequence 5' CGAAUCAGCUAUGUCG3' or a sequence complementary to said sequence, or fragments of the foregoing of between 10 to 16 nucleotides in length, wherein said oligonucleotide hybridizes to nucleic acid sequence of mycoplasma but not to nucleic acid sequence of another prokaryote or eukaryote.

37. A composition consisting essentially of a mycoplasma-specific probe, wherein said probe hybridizes with a particular nucleotide sequence, said particular nucleotide sequence comprises at least one of the following mycoplasma-specific sequence regions or a sequence region, of at least nine nucleotides, complementary to at least one of the following sequences: 5'AACACGTATC3', 5'CGAATCAGCTATGTCG3', 5'GAGGTT-AAC3', 5'ATCCGGATTTATT3', 5'TCTCAGTTCGGATTGA3', 5'AGGTGGTGCATGGTTG3', 5'TCCTGGCTCAGGAT3', 5'ATACATAGGT3', 5'AACTATGTGC3', 5'AATTTTTCACAATG3', 5'TCTCGGGTCT3', 5'TAGATATATG3', 5'AACACGUAUC3', 5'CGAAUCAGCUAUGUCG3', 5'GAGGUU-AAC3', 5'AUCCGGAUUUAUU3', 5'UCUCAGUUCGGAUUGA3', 5'AGGUGGUGCAUGGUUG3', 5'UCCUGGCUCAGGAU3', 5'AUACAUAGGU3', 5'AACUAUGUGC3', 5'AAUUUUUCACAAUG3', 5'UCUCGGGUCU3', 5'UAGAUAUAUG3', and a fragment of any one of the foregoing sequences or their complementary sequences, wherein said fragment comprises at least nine nucleotides, wherein T represents thymine, G represents guanine, A represents adenine, C represents cytosine, U represents uracil and - indicates a nucleotide deletion within the sequence, wherein said mycoplasma-specific probe hybridizes with the particular nucleotide sequence but not nucleotide sequences from eukaryotic or other prokaryotic organisms.

38. The composition of claim 37, wherein the mycoplasma-specific probe is labelled for detection.

39. A composition consisting essentially of a prokaryote-specific probe, wherein said probe hybridizes with a particular nucleotide sequence including at least one of the following prokaryotic sequence regions or a sequence region, of at least ten nucleotides, complementary to at least one of the following sequences: 5'ACGGGTGAGT3', 5'TAATACCGCAT3', 5'TACGGGAGGCAGCAGT3', 5'GTGGGGAGCAAA3', 5'AGGATTAGATACCCT3', 5'CCGTAAACGAT3', 5'GAATTGACGGGG3', 5'CCCGCACAAG3', 5'GGTGGAGCATGT3', 5'TGTTGGGTTAAGTCCCGCAACGA3', 5'GGGATGACGT3', 5'ACGTGCTACAATG3', 5'CTAGTAATCG3', 5'TGTACACACCGCCCGTCA3', 5'AAGTCGTAACAAGGTA3', 5'TGGATCACCTCCTT3', 5'ACGGGUGAGU3', 5'UAAUACCGCAU3', 5'UACGGGAGGCAGCAGU3', 5'GUGGGGAGCAAA3', 5'AGGAUUAGAUACCCU3', 5'CCGUAAACGAU3', 5'GAAUUGACGGGG3', 5'CCCGCACAAG3', 5'GGTGGAGCAUGU3', 5'UGUUGGGUUAAGUCCCGCAACGA3', 5'GGGAUGACGU3', 5'ACGUGCUACAAUG3', 5'CUAGUAAUCG3', 5'UGUACACACCGCCCGUCA3', 5'AAGUCGUAACAAGGUA3', 5'UGGAUCACCUCCUU3' and a fragment of any of the foregoing sequences or their complementary sequences, wherein said fragment comprises at least ten nucleotides, wherein T represents thymine, G represents guanine, A represents adenine, C represents cytosine and U represents uracil.

40. The composition of claim 39, wherein the prokaryote-specific probe is labelled for detection.

41. A composition consisting essentially of an oligonucleotide which under preselected hybridization conditions hybridizes to a mycoplasma-specific nucleic acid sequence but not to a non-mycoplasma-specific nucleic acid sequence.

42. The composition of claim 41, wherein the oligonucleotide comprises at least nine nucleotides.

43. The composition of claim 41, wherein the oligonucleotide comprises a section which is substantially complementary to the mycoplasma-specific nucleic acid sequence such as to allow the oligonucleotide to hybridize under said preselected hybridization conditions to the mycoplasma-specific nucleic acid sequence, said section comprises from nine to sixteen nucleotides.

44. A composition consisting essentially of a synthesized and isolated oligonucleotide which comprises a section substantially complementary to the nucleic acid sequence of a prokaryotic organism such that said section hybridizes under preselected hybridization conditions to the nucleic acid sequence of the prokaryotic organism but not to the nucleic acid sequence of a non-prokaryotic organism, said section being from nine nucleotides to twenty-three nucleotides.

45. The composition of claim 44, wherein the prokaryotic organism is a mycoplasma and the oligonucleotide hybridizes under said preselected hybridization conditions to a mycoplasma-specific nucleic acid sequence but not to a non-mycoplasma-specific nucleic acid sequence.

46. A composition consisting essentially of a synthesized and isolated oligonucleotide which comprises a section having a defined nucleic acid sequence substantially complementary to the nucleic acid sequence of a prokaryotic organism such that said section hybridizes under said preselected hybridization conditions to the nucleic acid sequence of the prokaryotic organism but not to the nucleic acid sequence of a non-prokaryotic organism.

47. A composition consisting essentially of an oligonucleotide which comprises a section having a defined nucleic acid sequence substantially complementary to the nucleic acid sequence of a mycoplasma such that said section hybridizes under said preselected hybridization conditions to the nucleic acid sequence of the mycoplasma but not to the nucleic acid sequence of an eukaryote or of another prokaryote.

48. A method for determining the presence of a prokaryotic organism in a medium comprising the steps of:
contacting the medium, which may contain a target nucleic acid sequence from said prokaryotic organism, with a synthesized and isolated oligonucleotide which under preselected hybridization conditions hybridizes with said target nucleic acid sequence but does not hybridize with non-target nucleic acid sequences in said medium; and
detecting, under said preselected hybridization conditions, the presence of said target nucleic acid sequence.

49. The method of claim 48 in which said preselected hybridization conditions are stringent.

50. The method of claim 48 in which said target nucleic acid sequence is a rRNA sequence.

51. The method of claim 48 in which said target nucleic acid sequence is a DNA sequence.

52. A method for determining the presence of a prokaryotic organism having a specified nucleic acid sequence, comprising the steps of:
contacting nucleic acid sequences from said prokaryotic organism with an oligonucleotide which under preselected hybridization conditions hybridizes with said specified nucleic acid sequence but does not hybridize with non-specified nucleic acid sequences; and
detecting the presence of any nucleic acid sequence with which said oligonucleotide hybridizes under said preselected hybridization conditions.

53. The method of claim 52 in which said preselected hybridization conditions are stringent.

54. A composition comprising a synthesized and isolated oligonucleotide sequence which is substantially complementary to a target nucleic acid sequence of a preselected prokaryotic organism but which is not substantially complementary to non-target nucleic acid sequences.

55. The composition of claim 54 in which said oligonucleotide sequence has at least nine nucleotides.

56. The composition of claim 54 in which said target nucleic acid sequence is a rRNA sequence.

57. The composition of claim 54 in which said target nucleic acid sequence is a DNA sequence.

58. A composition comprising a synthesized and isolated oligonucleotide which hybridizes under preselected hybridization conditions to a preselected nucleic acid sequence of a prokaryotic organism but not to non-selected nucleic acid sequences.

59. The composition of claim 58 in which said oligonucleotide has at least nine nucleotides.

60. The composition of claim 58 in which said hybridization conditions are stringent.

61. A composition comprising a synthesized and isolated oligonucleotide having at least nine nucleotides and which is substantially complementary to, and hybridizes under stringent hybridization conditions with, a target nucleic acid sequence of a preselected prokaryotic organism but does not hybridize with non-target nucleic acid sequences under said stingent hybridization conditions.

62. The composition of claim 61 in which said target nucleic acid sequence is a rRNA sequence.

63. The composition of claim 61 in which said target nucleic acid sequence is a DNA sequence.

* * * * *

UNITED STATES PATENT AND TRADEMARK OFFICE
CERTIFICATE OF CORRECTION

PATENT NO. : 5,851,767
DATED : December 22, 1998
INVENTOR(S) : Eric J. Stanbridge et al.

It is certified that error appears in the above-identified patent and that said Letters Patent is hereby corrected as shown below:

Title page,
Page 2, OTHER PUBLICATIONS, line 24, cancel "Bos" and insert --Bops--

Column 1, line 29, cancel "atypical" and insert --a typical--
Column 4, line 20, cancel "($1X10^{5-1X10^6}$ cells)" and insert --($1X10^5$ - $1X10^6$ cells)--

Claim 5, column 8, line 48, "cancel "Mollicutes" and insert --*Mollicutes*--
Claim 5, column 9, line 4, "cancel "Mollicutes" and insert --*Mollicutes*--
Claim 6, column 9, line 20 "cancel "Mycoplasma" and insert --*Mycoplasma*--
Claim 9, column 9, line 31, "cancel "Mollicutes" and insert --*Mollicutes*--
Claim 9, column 9, line 55, "cancel "Mollicutes" and insert --*Mollicutes*--
Claim 14, column 10, line 24 "cancel "Mycoplasma" and insert --*Mycoplasma*--
Claim 26, column 13, line 8, cancel ", sequence but not to a non-mycoplasma-specific nucleic acid sequence"
Claim 61, column 16, line 47, cancel "stingent" and insert --stringent--.

Signed and Sealed this

Eighteenth Day of May, 1999

Attest:

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO. : 5,851,767
DATED : December 22, 1998
INVENTOR(S) : Eric J. Stanbridge et al.

It is certified that error appears in the above-identified patent and that said Letters Patent is hereby corrected as shown below:

On the title page,

Item [56]   References Cited, U. S. Patent Documents

Please insert --4,851,330 7/1989 Kohne 435/6--

Signed and Sealed this

Eighth Day of June, 1999

Attest:

Q. TODD DICKINSON

Attesting Officer

Acting Commissioner of Patents and Trademarks